United States Patent
Wilson et al.

(10) Patent No.: US 10,258,904 B2
(45) Date of Patent: Apr. 16, 2019

(54) SYSTEM AND METHOD FOR REMOVING SULFUR FROM HYDROCARBON FLUIDS

(71) Applicants: Tom Wilson, Buffalo, SD (US); Dan A. Johnson, Dickinson, ND (US)

(72) Inventors: Tom Wilson, Buffalo, SD (US); Dan A. Johnson, Dickinson, ND (US)

(73) Assignee: BBL Holdings, LLC, Aberdeen, SD (US)

( * ) Notice: Subject to any disclaimer, the term of this patent is extended or adjusted under 35 U.S.C. 154(b) by 284 days.

(21) Appl. No.: 14/268,382

(22) Filed: May 2, 2014

(65) Prior Publication Data

US 2017/0072337 A1    Mar. 16, 2017

Related U.S. Application Data

(60) Provisional application No. 61/860,051, filed on Jul. 30, 2013.

(51) Int. Cl.
*B01D 19/00* (2006.01)
*B01D 53/14* (2006.01)
(Continued)

(52) U.S. Cl.
CPC ..... *B01D 19/0005* (2013.01); *B01D 53/1431* (2013.01); *B01D 53/1468* (2013.01);
(Continued)

(58) Field of Classification Search
CPC ...... B01D 5/0027; B01D 5/003; B01D 5/006; B01D 19/00; B01D 19/0005;
(Continued)

(56) References Cited

U.S. PATENT DOCUMENTS 2,729,590 A    1/1956  Bishop
3,208,930 A    9/1965  Andrassy
(Continued)

FOREIGN PATENT DOCUMENTS

EP    2770041    8/2014

OTHER PUBLICATIONS

"Safe, Cost-effective Onsite Removal of H2S from Crude Oil and Produced Water", S2S, LLC, pp. 1-7, web page www.sourtosweet.net, download date May 30, 2014.
(Continued)

*Primary Examiner* — Lucas A Stelling
(74) *Attorney, Agent, or Firm* — Jeffrey A. Proehl; Woods, Fuller, Shultz & Smith, P.C.

(57) ABSTRACT

An apparatus for removing sulfur from a hydrocarbon liquid may comprise a tank with a chamber, a barrier in the chamber forming at least a partial barrier to liquid flow with a gap defined therein, a gas distribution manifold for introducing the gas into the liquid, and a gas conversion structure defining an interior in fluid communication with the chamber. The gas conversion structure may include a conversion tube defining a tube interior in fluid communication with the chamber, an air injection device configured to inject air into the tube interior and draw gas from the chamber, a water injection device configured to inject water into the tube interior to create a mist of water in the tube interior to contact the gas from the chamber of the tank, and a fluid drain configured to drain fluid from the tube interior.

21 Claims, 5 Drawing Sheets

(51) Int. Cl.
*B01D 53/18* (2006.01)
*B01D 53/52* (2006.01)
*C07C 7/00* (2006.01)
*C10G 31/00* (2006.01)

(52) U.S. Cl.
CPC .......... *B01D 53/185* (2013.01); *B01D 53/52* (2013.01); *C07C 7/005* (2013.01); *C10G 31/00* (2013.01); *C10G 2300/202* (2013.01)

(58) Field of Classification Search
CPC .......... B01D 53/1431; B01D 53/1462; B01D 53/1468; B01D 53/18; B01D 53/185; B01D 53/48; B01D 53/485; B01D 53/52; B01D 53/523; B01D 53/526; B01D 53/38; B01D 53/40; B01D 53/44; B01D 17/00; C07C 7/005
See application file for complete search history.

(56) References Cited

U.S. PATENT DOCUMENTS

| | | | |
|---|---|---|---|
| 3,691,732 A * | 9/1972 | Richards | F23G 7/08 261/8 |
| 3,822,341 A | 7/1974 | Smith | |
| 5,023,064 A * | 6/1991 | Burgess | B01D 53/34 423/243.08 |
| 5,387,344 A | 2/1995 | McCombs | |
| 5,405,435 A | 4/1995 | Bekedam | |
| 6,080,320 A | 6/2000 | Von Phul | |
| 6,123,750 A * | 9/2000 | Espinal | B01D 19/0005 261/117 |
| 6,306,288 B1 | 10/2001 | Pittman | |
| 7,678,263 B2 | 3/2010 | Mock | |
| 9,364,773 B2 | 6/2016 | Morris | |
| 2004/0178152 A1 | 9/2004 | Morse | |
| 2007/0175796 A1 | 8/2007 | Mock | |
| 2008/0174033 A1* | 7/2008 | Duesel | B01D 1/0058 261/121.1 |
| 2012/0273339 A1 | 11/2012 | Whyatt | |
| 2012/0273393 A1 | 11/2012 | Whyatt | |
| 2013/0026062 A1 | 1/2013 | Al-Shahrani | |
| 2013/0310468 A1 | 11/2013 | Greer | |
| 2014/0238902 A1 | 8/2014 | Morris | |

OTHER PUBLICATIONS

"Treat Sour Oil and Water Safely with the S2S Hydrogen Sulfide Removal Technology", brochure, Sour to Sweet, Denver, CO, date unknown.

* cited by examiner

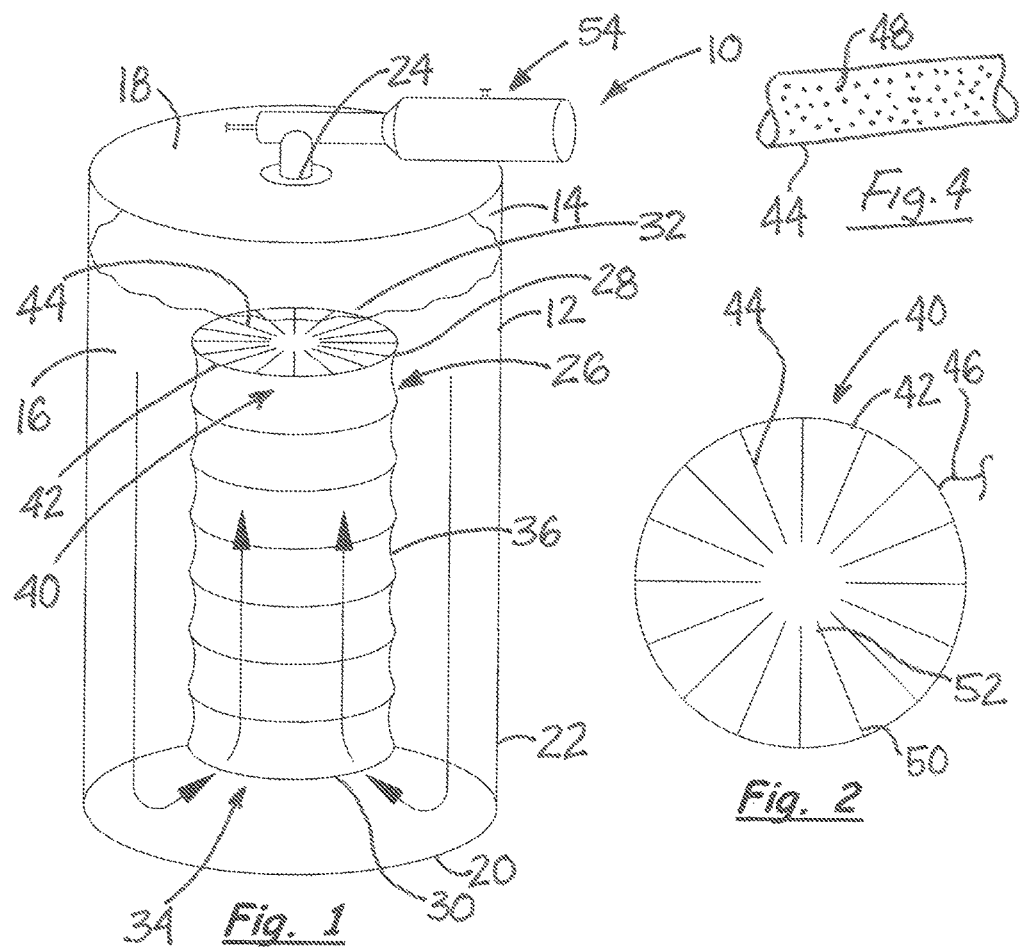
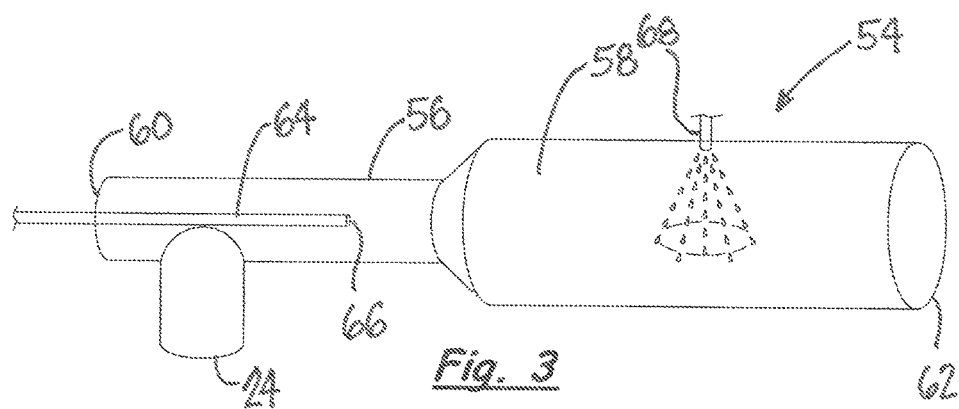

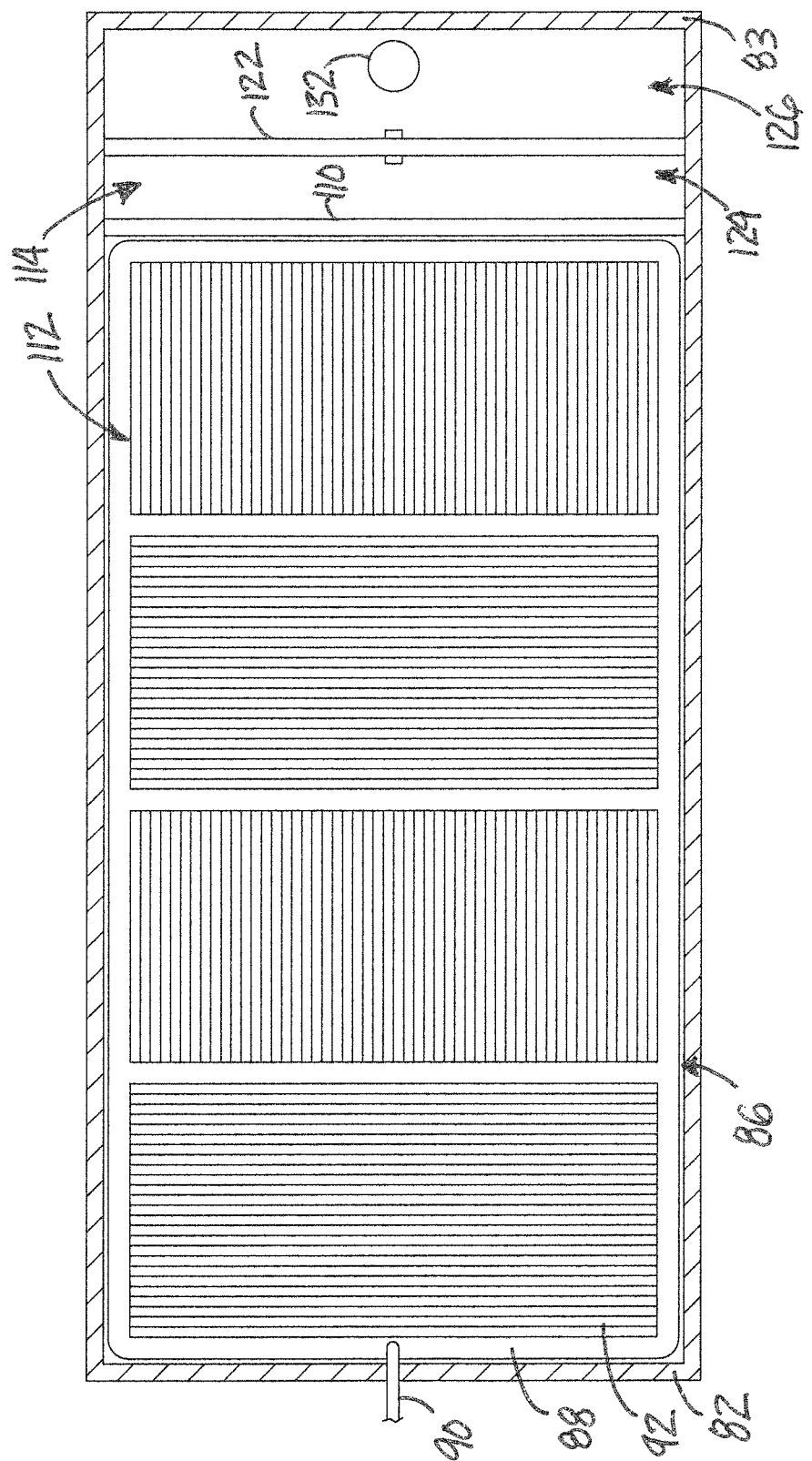

SYSTEM AND METHOD FOR REMOVING SULFUR FROM HYDROCARBON FLUIDS

REFERENCE TO RELATED APPLICATIONS

This application claims the priority of U.S. provisional patent application No. 61/860,051, filed Jul. 30, 2013, which is incorporated by reference in its entirety.

BACKGROUND

Field

The present disclosure relates to methods and systems for removing substances such as sulfur and sulfur-containing compounds from hydrocarbon compounds, and more particularly pertains to a new system and method for removing sulfur from hydrocarbon fluids that can be performed in a relatively simple and inexpensive manner.

SUMMARY

In some aspects, the present disclosure relates to an apparatus for removing sulfur from a hydrocarbon liquid, and may comprise a tank having an interior defining a chamber configured to hold a liquid, with the tank including an upper wall and a lower wall. The apparatus may also comprise a barrier in the chamber forming at least a partial barrier to liquid flow in the chamber, with at least a portion of the barrier extending substantially vertically in the chamber and a gap being defined between the lower wall of the tank and a lower portion of the barrier. The apparatus may further include a gas distribution manifold for introducing the gas into the liquid and being positioned in the chamber for being submerged in liquid positioned in the chamber. At least a portion of the gas distribution manifold may be perforated with holes to permit gas in an interior of the manifold to exit the manifold. The apparatus may also comprise a gas conversion structure defining an interior in fluid communication with the chamber of the tank. The gas conversion structure may include a conversion tube defining a tube interior and having an inlet end and an outlet end, with the tube interior being in fluid communication with the chamber of the tank, and an air injection device configured to inject air into the tube interior of the conversion tube and draw gas from the chamber of the tank. The gas conversion structure may also include a water injection device configured to inject water into the tube interior of the injection tube to create a mist of water in the tube interior to contact the gas from the chamber of the tank, and a fluid drain configured to drain fluid from the tube interior.

In other aspects, the disclosure relates to a method of removing sulfur from a hydrocarbon liquid may include providing a quantity of a hydrocarbon liquid in a tank with a space above the liquid, creating sulfur-containing gases from sulfur in the hydrocarbon liquid, capturing the sulfur-containing gases created, and removing sulfur from the sulfur-containing gases.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, as well as the particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein:

FIG. 1 is a schematic perspective view of a new system for removing sulfur from hydrocarbon fluids according to the present disclosure.

FIG. 2 is a schematic top view of an aspect of the system including a gas distribution manifold, according to an illustrative embodiment.

FIG. 3 is a schematic perspective view of an aspect of the system including a gas conversion structure, according to an illustrative embodiment.

FIG. 4 is a schematic side view of an aspect of the system including a portion of one of the gas diffusing pipes, according to an illustrative embodiment.

FIG. 8 is a schematic sectional view of an apparatus with another configuration generally corresponding to the embodiments shown in FIG. 6, with the section being taken along a horizontal plane.

DETAILED DESCRIPTION

Figure 5:
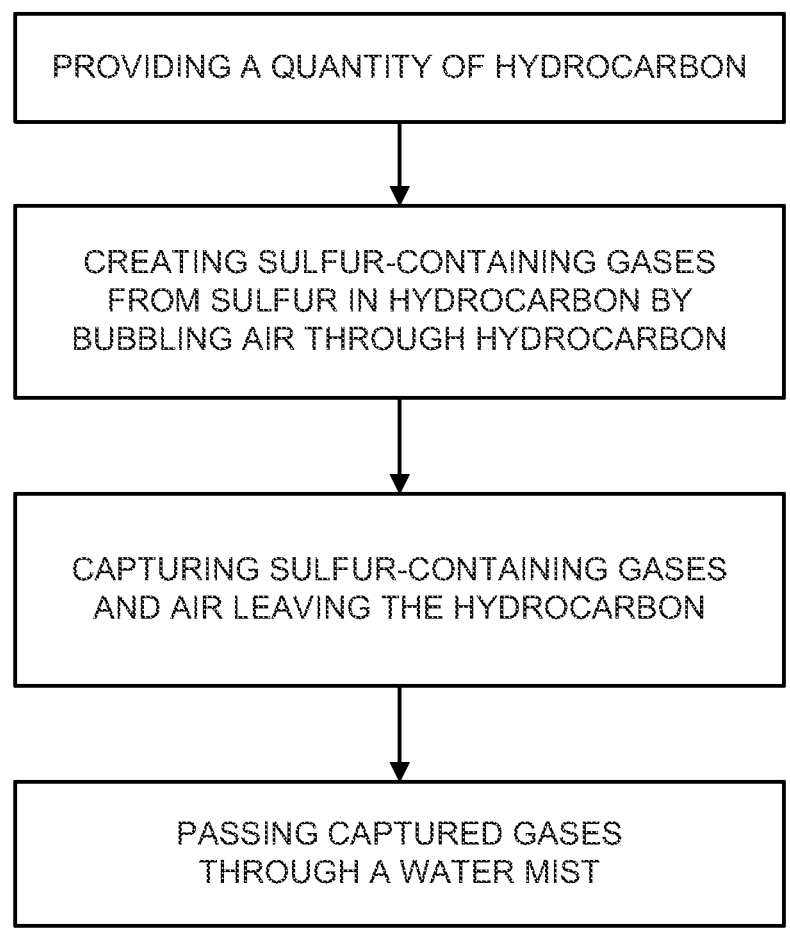
FIG. 5 is a schematic flow diagram of a method of the disclosure, according to an illustrative implementation.

With reference now to the drawings, and in particular to FIGS. 1 through 8 thereof, a new system and method for removing sulfur from hydrocarbon fluids embodying the principles and concepts of the disclosed subject matter will be described.

In one aspect, the disclosure relates to an apparatus 10 for removing sulfur from a hydrocarbon fluid or liquid. The apparatus 10 may be used to treat batches or relatively fixed quantities of liquid, and may also be used in a continuous manner to treat a flow of the liquid.

The apparatus may include a tank 12 which holds the liquid quantity being treated. The tank 12 has an interior 14 that defines a treatment chamber 16. The tank 12 may have an upper wall 18, a lower wall 20 and a peripheral wall 22 that extends between the upper and lower walls. The upper wall 18 may have a vent opening 24 that is able to communicate with the space at the top of the chamber and the gases located there, particularly when the interior of the chamber is only partially filled with the liquid and the upper portion of the chamber is empty of the liquid and contains air as well as any gases that escape from the liquid in the tank.

In some embodiments, the apparatus 10 may also include a barrier that comprises a duct 26 that is positioned in the chamber 16 of the tank. The duct has an upper end 28 and a lower end 30, with the duct having an upper opening 32 at the upper end 28 and a lower opening 34 at the lower end. The duct is configured to permit the liquid to enter the lower opening of the duct, and in some embodiments the lower end 30 may be positioned adjacent to the lower wall 20 of the tank with a separation between the lower end of the duct and the lower wall of the tank. The duct may have a perimeter wall 36 extending between the upper end 28 and the lower end 30 of the duct. In some embodiments, the perimeter wall 36 may be flexible, and may also be collapsible, and may have a substantially circular horizontal cross section.

The apparatus 10 may also include a gas distribution manifold 40 configured to introduce or infuse a gas, such as atmospheric air, into the liquid contained in the chamber of the tank. The manifold 40 may be positioned such that it is located below the surface of the liquid in the tank chamber. In some embodiments, the manifold is positioned approximately 24 to 30 inches below the surface of the liquid, and in other embodiments the manifold is located lower in the chamber, and may be positioned adjacent to the lower wall of the tank. The manifold 40 may be mounted on the duct 26, and may be positioned toward the upper end of the duct. In some of the most preferred embodiments, the manifold 40 is located at the upper opening 32 of the duct and is positioned across the upper opening such that liquid moving through the upper opening also passes through the manifold.

In some embodiments, the gas distribution manifold 40 may include a gas distribution pipe 42 and at least one gas diffusing pipe 44, although in some of the most preferred embodiments, a plurality of gas diffusing pipes are employed. One highly effective embodiment of the manifold 40 includes a distribution pipe which extends along a closed path, and the path may be circular with a size and shape that may correspond to the size and shape if the perimeter wall 36 of the duct at the upper opening. The gas distribution pipe 42 may have an inlet 46 for receiving the gas into the manifold, which in turn may be placed into communication with a source of the gas, typically air, and the air may be supplied to the manifold at various suitable pressures. The pressure at which the gas is supplied may vary, and one factor in selecting a suitable gas pressure is the specific gravity of the liquid into which the gas is being injected. For relatively higher specific gravity liquids, relatively lower pressures may be employed such as, for example, 15 pounds per square inch (psi), and for relatively lower specific gravity liquids, relatively higher pressures may be employed, such as 150 psi. Illustratively, a range of pressures from approximately 10 psi to approximately 175 psi may be employed, and in some embodiments a range from approximately 15 psi to approximately 150 psi may be employed. In some further embodiments, a pressure of approximately 30 psi to approximately 70 psi may be employed, and in one illustrative implementation the pressure is approximately 50 psi.

The one or more gas diffusing pipes 44 may be mounted on and in fluid communication with the gas distribution pipe 42. At least a portion of the gas diffusing pipes 44 may be perforated with holes to permit gas in the interior of the diffusing pipe to exit the pipe through the perforations. In some of the more preferred embodiments, the perforations extend along a portion of the pipe 44 that is greater than half of the length of the pipe 44, and may be greater than three-quarters of the length, and in some embodiments may be substantially the entire length of the pipe 44. Each of the diffusing pipes 44 may have a proximal end 50 that is connected to the distribution pipe and a distal end 52 that is closed and is positioned relatively away from the distributing pipe 42. The gas diffusing pipes 44 may radiate from the gas distribution pipe, and may radiate inwardly from the distributing pipe. In the illustrative embodiments, the gas diffusing pipes radiate inwardly from the substantially circular distribution pipe toward a center of the manifold much the same as spokes radiate inwardly from the rim of a wagon wheel. The pipes 44 may thus be positioned across the upper opening 32 of the duct to be in communication with liquid located at and moving through the upper opening. As an example, one manifold has a gas distribution pipe with a diameter of approximately 6 feet.

The perforations or holes in the walls of the gas diffusing pipes 44 may be relatively very small to produce very small bubbles with relatively high surface area as compared to bubble of air having a larger size. It has been discovered that it is advantageous to reduce the size of the perforations or holes as the specific gravity of the liquid increases. Liquids with relatively high specific gravity may benefit from the use of holes with a measurement of approximately 0.003 inches, and liquids with relatively lower specific gravities may benefit from relatively larger holes with sizes as high as approximately 0.01 inches. In some of the most preferred embodiments of the pipes 44, the size of the perforations is approximately 0.007 inches or less. In other embodiments, the size of the perforations may be approximately 0.01 inch or less, although holes of sizes somewhat larger may be suitably used.

The apparatus 10 may further include a gas conversion structure 54 which may be in fluid communication with the vent opening 24 of the tank such that the structure 54 is in fluid communication with the upper portion of the tank chamber and the gases therein. The gas conversion structure 54 may comprise a conversion tube 56 that defines a tube interior 58 and has an inlet end 60 and an outlet end 62. The tube interior 58 may be in fluid communication with the vent opening 24 of the tank toward the inlet end 60 of the conversion tube, and may include a short pipe extending between the vent opening of the tank and the a hole in the tube to create the free flow of gases from the tank chamber to the tube interior. Preferably, the cross sectional area of the tube interior 58 at the outlet end 62 is relatively greater than the cross sectional area of the tube interior at the inlet end 60, and the decreased cross sectional area tends to cause a slight vacuum at the inlet end (and the vent opening 24 as well as the head space of the chamber in communication with the inlet end), as gas moves from the inlet end to the outlet end.

The gas conversion structure 54 may include an air injection device 64 that is configured to inject air into the tube interior 58 of the conversion tube 56 to help induce a gas flow into and through the conversion tube. The air injection device 64 may have a port 66 that is positioned in the tube interior and is in fluid communication with the tube interior toward the inlet end 60 of the conversion tube. Illustratively, the air injection device 64 may inject air into the tube interior at approximately 100 psi to approximately 150 psi, and in one illustrative implementation is at approximately 125 psi.

A water injection device 68 may be included in the gas conversion structure 54 for injecting a mist of fluid, such as water, into the tube interior 58 of the conversion tube 56 to mix the water with the gases from the tank chamber. The water injection device 68 may produce at least one stream of water droplets into the tube interior, and preferably creates a plurality of streams of droplets. In one highly preferred embodiment, the device 68 produces three streams of water droplets into the tube interior. The water injection device 68 may produce one or more streams in a downward direction into the tube interior, the water injection device being located toward the tube outlet end with respect to the port of the air injection device and the inlet end. The gas conversion structure 54 may include a fluid drain for draining away the fluid from the tube interior, which may include water and the residual sulfate.

Another aspect of the disclosure relates to a method or process for removing sulfur from a hydrocarbon liquid. The process may include providing a quantity of a hydrocarbon liquid that may contain sulfur in some form (such as sulfur-containing compounds), and this step may include placing the liquid in a tank with a space above the liquid in the chamber of the tank.

Another portion of the process may include creating sulfur-containing gasses from the sulfur and sulfur-containing compounds in the hydrocarbon liquid. This may include injecting air into the hydrocarbon liquid to create sulfur-containing gases such as hydrogen sulfide, and injecting the air may be performed by creating a plurality of air bubbles in the liquid. A highly suitable manner of performing this act is through the positioning of the gas distribution manifold in the liquid and moving air through the manifold and out through the perforations. The air may be pressurized to force the air into the liquid through the holes.

In some implementations, the manifold may be positioned adjacent to the upper opening of a duct such as is described herein. In such implementations, the infusion of the air may tend to induce movement in the fluid, with the fluid being induced to move out of the upper opening of the duct, thus tending to pull fluid into the lower opening of the duct, and in turn pulling fluid from the tank located outside the duct (but into the chamber) downwardly toward the lower opening. In other implementations, the manifold may be utilized in a tank without the duct, and may be positioned below the liquid surface such as adjacent to the lower wall of the tank. Such an implementation may be more suitable for use in relatively smaller tanks and quantities of the liquid.

Another portion of the process includes capturing gases from a space above the hydrocarbon liquid, including the air being infused into the tank and the hydrogen-containing gases created, such as the hydrogen sulfide generated. The capture may be effected by inducing a flow of the gases from the space above the liquid and into a structure such as the gas conversion structure described herein.

The captured gases may be passed through a mist of water droplets, and the captured gases may be passed through the gas conversion structure. A flow of the captured gases may be induced through the structure, and may be accomplished by injecting air into the structure to create a flow of air through the structure and inducing gas flow from the tank and into the structure. The process may also include providing the structure with an increasing cross sectional area to induce a vacuum in the flow of air and captured gases passing through the structure. A mist of water may be created in the flow of air and captured gases, and droplets of water may be sprayed from one or more nozzles into the flow of air and gases. Residual water and sulfur compounds in the water may be removed from the structure.

Figure 6:
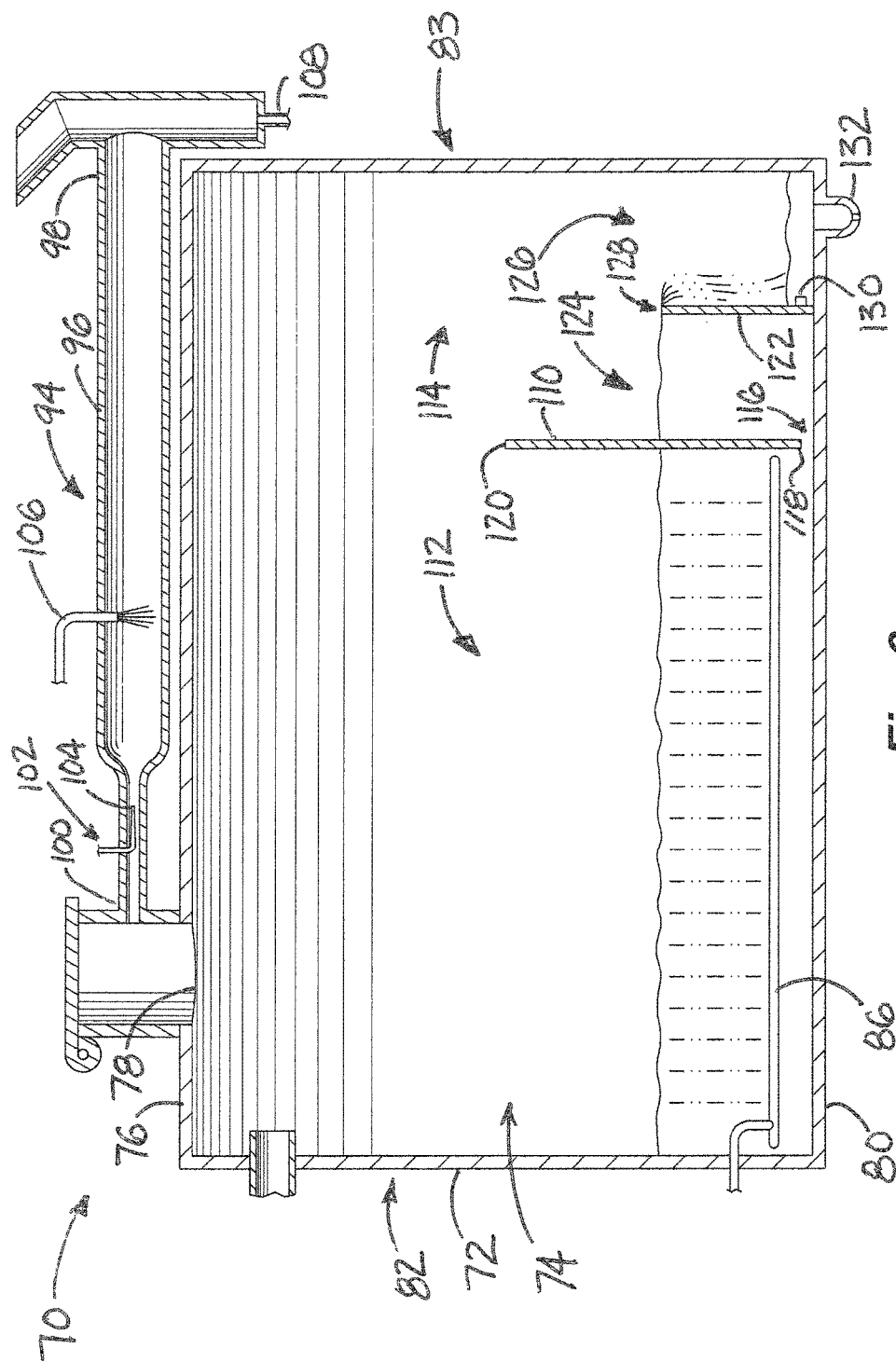
FIG. 6 is a schematic sectional view of the apparatus according to other embodiments of the disclosure, with the section being taken along a vertical plane.
Figure 7:
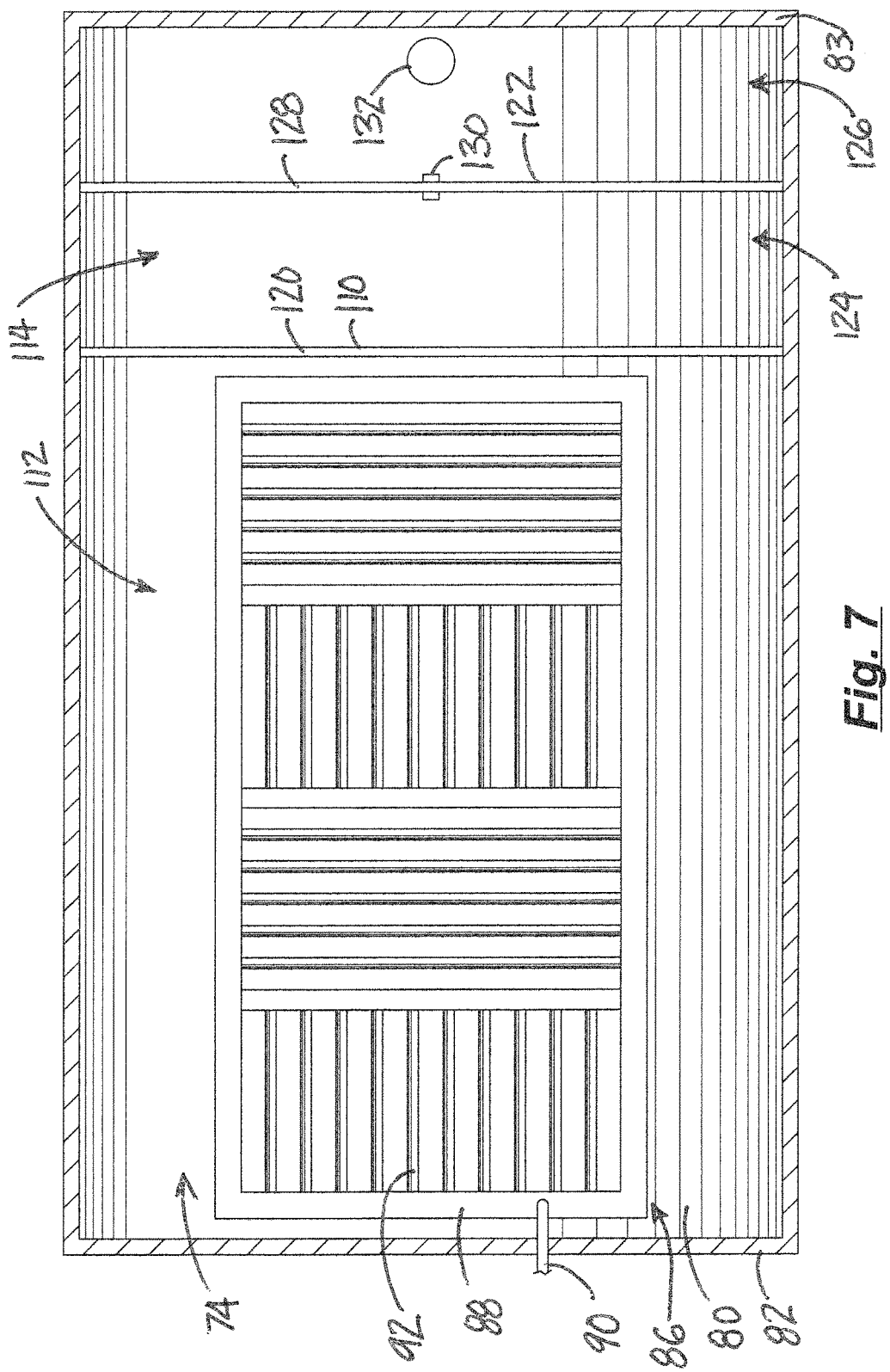
FIG. 7 is a schematic sectional view of an apparatus with a configuration generally corresponding to the embodiments shown in FIG. 6, with the section being taken along a horizontal plane.

Other embodiments of the apparatus may include many similar but not identical aspects of the embodiments disclosed above. As shown in FIGS. 6 through 8, the embodiments of the apparatus 70 are also capable of removing contaminants, such as sulfur, from a liquid such as a hydrocarbon liquid, and may be more suitable for performing removal in a continuous manner (e.g., from a continuous or substantially continuous flow of the liquid). The embodiments also include a tank 72 which has an interior defining a chamber 74 and which has an upper wall 76 and an opening 78. The opening may be designed as a manway to provide access to the chamber of the tank when needed, although this configuration is not critical. The tank 72 may also have a lower wall 80, In some embodiments, the tank 73 is elongated in a horizontal direction, rather than in the vertical direction. The elongated shape tank 72 may have a first end 82 and a second end 83, and the first end may be an inlet end and the second end may be an outlet end. The tank may have a substantially cylindrical shape, with the cylindrical shape being elongated along a horizontal axis and the tank may have an elongated substantially cubical or three dimensional rectangular shape which may be elongated in the horizontal direction.

The apparatus 70 may also include a gas distribution manifold 86 for introducing the gas into the liquid in the tank. The gas distribution manifold 86 may be mounted or positioned in the interior of the tank for submergence in the liquid when liquid is positioned in the tank chamber 74. The manifold 86 may be located relatively low in the chamber of the tank, such as close to the lower wall. In some of the most preferred embodiments, the manifold 86 extends in a generally horizontal plane, but may be slanted to some degree, or have portions that are substantially horizontal and portions that are not horizontal. The manifold 86 may extend from one side wall of the tank to another side wall, although this is not critical, although maximizing the amount of air moved into the liquid through the manifold may make the processing of the liquid faster and more complete, so maximizing the size of the manifold (and thus the number of perforations in the manifold) for the size of tank may be advantageous.

The manifold 86 may include a gas distribution pipe 88, and the pipe 88 may extend along a closed path with an inlet 90 for receiving the gas. The gas distributing pipe 88 may extend along a substantially rectangular path, although the shape of the path is not critical to the operation of the apparatus. It is desirable to have the manifold 86, and any distribution pipe 88 that forms the perimeter of the manifold, to extend across the chamber as far as practicable. For example, as shown in FIG. 8 showing the cross section of a tank having a substantially rectangular cross sectional shape in a vertical plane, the manifold extends to the long side walls while as shown in FIG. 7 showing the cross section of a tank having a substantially circular cross sectional shape in vertical plane, the manifold extends a more limited distance horizontally toward the sides due to the wall of the tank gradually sloping upward from the lower most point.

The gas distribution manifold 86 may also include at least one gas diffusing pipe 92 mounted on and in fluid communication with the gas distribution pipe 88, with at least a portion of the gas diffusing pipe being perforated with holes to permit gas in the interior of the diffusing pipe to exit the pipe. The diffusing pipe 92 may have one or both ends fixed to and in communication with the distribution pipe 88. A plurality of the gas diffusing pipes 92 may be connected to the distribution pipe, and groups of the diffusing pipes may be oriented in different directions, such as in perpendicular directions.

The apparatus 70 may also include a gas conversion structure 94 in fluid communication with the interior of the tank 72 via the opening 78 of the tank. The gas conversion structure may comprise a conversion tube 96 defining a tube interior in fluid communication with the opening 78 of the tank. The conversion tube may have a cross sectional area at an outlet end 98 that is relatively greater than a cross sectional area 100 of the interior at the inlet end. The gas conversion structure may also include an air injection device 102 that is configured to inject air into the interior of the conversion tube, and may have a port 104 in fluid communication with the inlet end of the conversion tube. The gas conversion structure may also include a water injection device 108 that is configured to inject a mist of water into the interior of the injection tube, and may produce at least one stream of water droplets into the tube interior. The gas conversion structure may also include a fluid drain 108 configured to drain water and sulfate as well as other substances precipitated out of the gases exiting the chamber.

The apparatus 70 may also utilize a first interior wall 110 as a barrier positioned in the interior of the tank 72 and which may extend across a portion of the chamber of the tank. The first interior wall 110 may divide the chamber 74 into a first chamber portion 112 and a second chamber portion 114, although the division may not be a complete isolation of the portions 112, 114 from each other. The first chamber portion 112 may be located toward the inlet end 82 of the tank, and the second chamber portion may be located toward the outlet end 83 of the tank. The first interior wall 110 may extend upwardly from the lower wall 80 toward the upper wall 76. A gap 116 may be located between a portion of the first interior wall 110 and the lower wall 80, and the first interior wall may have a lower edge 118 that is spaced from the lower wall 80 to form the gap 116. The first interior wall 110 may have an upper edge 120 that is spaced from the upper wall 76. In some embodiments, the first interior wall 110 may extend approximately 40% to approximately 60% of a distance between the lower wall 80 and the upper wall 76, and in some embodiments the first interior wall 110 may extend approximately half of a distance between the upper wall and the lower wall. The first interior wall may be positioned a distance from the inlet end of the tank that is about 50 percent to 80 percent of the total length of the chamber, so that the first chamber portion is greater in length (and corresponding volume size) than the second chamber portion.

The apparatus 70 may also include a second interior wall 122 in the interior of the tank 72 and which may extend across a portion of the chamber 74 of the tank. The second interior wall 122 may divide the second chamber portion 114 into a first subchamber 124 and a second subchamber 126, although the division between the subchambers may not create a complete separation. The first subchamber 124 may be in fluid communication with the first chamber portion 112 through the gap 116. The second interior wall 122 may extend upwardly from the lower wall 80 toward the upper wall 76 of the tank. The first subchamber 124 may be positioned between the second interior wall 122 and the first interior wall 110. The second subchamber may be located between the second interior wall and the second (outlet) end 83 of the tank. The height of a top edge 128 of the second interior wall above the lower wall may be less than the height of the top of the first interior wall above the lower wall 80, and the height of the second interior wall may be less than half of the height of the first interior wall. A closable drain hole 130 may be formed in the second interior wall toward a bottom of the second interior wall for draining fluid from the bottom of the tank.

A sump 132 may be formed in the lower wall 80 of the tank for draining the liquid from the tank, including liquid that has passed over the second interior wall into the second subchamber.

The gas distribution manifold 86 may be positioned at a height from the lower wall that is less than the height of the upper edge 120 of the first interior wall, and as a result below the surface of the liquid in the chamber of the tank. In some embodiments, the position of the gas distribution manifold with respect to the upper surface of the lower wall may be that the manifold rests upon the upper surface of the lower wall, although some separation between the manifold and the lower wall is often desirable so that the manifold does not rest in any accumulation of solids one the upper surface of the lower wall. In some embodiments, the manifold may be up to approximately 12 inches from the lower wall upper surface, and may be approximately 3 inches to approximately 12 inches from the lower wall, and may be approximately 3 inches to 8 inches from the lower wall upper surface.

In an illustrative embodiment, the tank has a chamber with a height of approximately 8 feet, a width of approximately 8 feet, and a length of approximately 16 feet. The first interior wall may be approximately 12 feet from the inlet end. The first interior wall may have a height measured from the lower wall of approximately 4 feet, and the gap formed beneath the first interior wall may be approximately 2 inches. The height of the second interior wall may be approximately 18 inches. The second interior wall may be located approximately 14 feet from the inlet wall.

Liquid that enters the chamber 74 of the tank moves into the first chamber portion 112 and is exposed to the gas bubbles escaping from the perforations from the gas diffusing pipes 92 of the gas distribution manifold. The liquid may move through the gap 116 into the first subchamber and fill the first subchamber to the top edge 128 of the second interior wall. As the liquid fills the first chamber portion and then fills the first subchamber of the second chamber portion, the liquid moves over the second interior wall into the second subchamber. As the liquid moves over the top edge of the second interior wall, any gas bubbles that remain entrained in the liquid are caused to move out of the liquid as the thin flow of liquid passes over the wall. As the liquid moves into the second subchamber it drains from the tank chamber through the sump 132.

In most of the preferred embodiments, utilizing atmospheric or environmental air as the gas moving through the liquid has benefits of ready availability, although it is conceivable that other gases may be utilized. It has been recognized by the applicants that air that is heated to a temperature that is higher than the temperature of atmospheric air may be more suitable for processing some wastes, and air at temperatures up to approximately 100 degrees F. to approximately 150 degrees F. or more may be utilized, typically by heating air drawn from the atmosphere before introducing the air into the gas distribution manifold.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that the steps shown in the drawing figures may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

We claim:

1. An apparatus for removing sulfur from a hydrocarbon liquid, comprising:
    a tank having an interior defining a chamber configured to hold a liquid, the tank including an upper wall and a lower wall;
    a barrier in the chamber forming at least a partial barrier to liquid flow in the chamber, at least a portion of the barrier extending substantially vertically in the chamber, a gap being defined between the lower wall of the tank and a lower portion of the barrier;
    a gas distribution manifold for introducing the gas into the liquid, the gas distribution manifold being positioned in the chamber for being submerged in liquid positioned in the chamber, at least a portion of the gas distribution manifold being perforated with holes to permit gas in an interior of the manifold to exit the manifold;
    a gas conversion structure in fluid communication with the chamber of the tank, the gas conversion structure including:
        a conversion tube defining a tube interior and having an inlet end and an outlet end, the tube interior being in fluid communication with the chamber of the tank;
        an air injection device configured to inject air into the tube interior of the conversion tube in a manner inducing a gas flow in the tube interior such that gas is drawn from the chamber of the tank;
        a water injection device configured to inject water into the tube interior of the injection tube to create a mist of water in the tube interior to contact the gas from the chamber of the tank; and
        a fluid drain configured to drain fluid from the tube interior.

2. The apparatus of claim 1 wherein the tube interior has a cross sectional area defined in a plane oriented substantially perpendicular to a direction of gas flow through the tube interior; and
    wherein the cross sectional area of the tube interior at the outlet end of the conversion tube is greater than a cross sectional area of the tube interior at the inlet end of the conversion tube.

3. The apparatus of claim 1 wherein the air injection device has a port in fluid communication with the tube interior at a location relatively closer to the inlet end of the conversion tube and the water injection device injects water into the tube interior at a location relatively closer to the outlet end of the tube.

4. The apparatus of claim 1 wherein the barrier comprises a duct positioned in the chamber of the tank, the duct having an upper end with an upper opening and a lower end with a lower opening.

5. The apparatus of claim 4 wherein the lower end of the duct is positioned adjacent to but spaced from the lower wall of the tank by the gap.

6. The apparatus of claim 1 wherein the barrier includes a first interior wall in the interior of the tank extending across a portion of the chamber of the tank to divide the chamber into a first chamber portion and a second chamber portion, the gas distribution manifold being located in the first chamber portion.

7. The apparatus of claim 6 wherein the first interior wall extends upwardly from the lower wall toward the upper wall, the gap being located between a portion of the first interior wall and the lower wall.

8. The apparatus of claim 6 additionally comprising a second interior wall in the interior of the tank and extending across a portion of the chamber of the tank, the second interior wall dividing the second chamber portion into a first subchamber and a second subchamber.

9. The apparatus of claim 8 wherein the first subchamber is in fluid communication with the first chamber portion through the gap, the first subchamber being positioned between the second interior wall and the first interior wall.

10. The apparatus of claim 8 wherein the second interior wall extends upwardly from the lower wall of the tank toward the upper wall of the tank, a height of a top edge of the second interior wall above the lower wall being less than a height of a top edge of the first interior wall above the lower wall such that liquid moving from the first chamber to the second subchamber moves through the gap under the first interior wall and over the top edge of the second interior wall.

11. The apparatus of claim 6 wherein the gas distribution manifold is positioned in the first chamber portion at a height above the lower wall that is less than a height of an upper edge of the first interior wall above the lower wall.

12. The apparatus of claim 1 wherein the gas distribution manifold comprises at least one gas diffusing pipe with the holes formed therein, the at least one gas diffusing pipe being oriented in a substantially horizontal direction.

13. The apparatus of claim 1 wherein the water injection device is configured to produce a stream of water in a downward direction into the tube interior of the conversion tube.

14. The apparatus of claim 1 wherein the air injection device and the water injection device are configured such that the air is injected into the tube interior by the air injection device separately of the water injected into the tube interior by the water injection device.

15. The apparatus of claim 1 wherein the air injection device and the water injection device are configured such that air is injected into gas flow in the tube interior by the air injection device before water is injected into gas flow in the tube interior by the water injection device.

16. The apparatus of claim 1 wherein the air injection device is configured to inject air into the tube interior in a same direction of movement as the gas flow from the chamber of the tank to effectively induce the gas flow in the tube interior.

17. The apparatus of claim 1 wherein the air injection device includes a conduit with a section positioned in the tube interior, the section being elongated along an axis oriented substantially parallel to a direction of gas flow through the tube interior, the tube terminating in a port through which the air is injected into the tube interior, the port being located downstream from the secion of the conduit such that air is injected in a same direction of movement as the gas flow.

18. The apparatus of claim 1 wherein the tube interior has an inlet portion located toward the inlet end of the conversion tube and an outlet portion located toward the outlet end of the conversion tube;
   wherein the tube interior has a cross sectional area defined in a plane oriented substantially perpendicular to a direction of gas flow through the tube interior;
   wherein the cross sectional area of the tube interior at the outlet portion of the conversion tube is greater than a cross sectional area of the tube interior at the inlet portion of the conversion tube;
   wherein the air injection device is configured to inject air into the tube interior in the inlet portion of the tube interior; and
   wherein the water injection device is configured to inject water into the tube interior in the outlet portion of the tube interior.

19. The apparatus of claim 18 wherein the air injection device includes a conduit with a section positioned in the tube interior, the section terminating in a port through which the air is injected into the tube interior, the port being located in the inlet portion of the tube interior.

20. The apparatus of claim 1 wherein the gas conversion structure is configured such that gas flow through the tube interior of the conversion tube moves along a substantially horizontal axis and air is injected into the gas flow in a substantially horizontal direction; and
   wherein the gas conversion structure is configured such that water injected by the water injection device moves downwardly in the tube interior of the conversion tube.

21. An apparatus for removing sulfur from a hydrocarbon liquid, comprising:
   a tank having an interior defining a chamber configured to receive a liquid, the tank including an upper wall and a lower wall, the tank having a liquid inlet closer to the upper wall than the lower wall to permit liquid entering the chamber through the liquid inlet to fall toward the lower wall, a liquid outlet being located closer to the lower wall than the upper wall to permit the liquid to exit the chamber;
   a gas distribution manifold for introducing a gas into the chamber, the gas distribution manifold being positioned toward the lower wall of the chamber such that the gas exiting the manifold contacts liquid having entered the chamber through the liquid inlet, at least a portion of the gas distribution manifold being perforated with holes to permit the gas in an interior of the manifold to exit the manifold, the tank having an upper opening for venting from the chamber the gas exiting the gas distribution manifold and moving upwardly through the liquid as a gas stream;
   a barrier in the chamber forming at least a partial barrier to movement of liquid through the chamber, at least a portion of the barrier being positioned between the liquid inlet and the liquid outlet to promote contact between the liquid moving between the liquid inlet and outlet and the gas exiting the gas distribution manifold, a gap being defined between the lower wall of the tank and a lower portion of the barrier; and
   wherein the liquid inlet of the tank is located at a vertical level higher than an uppermost extent of the barrier and the liquid outlet of the tank is located at a vertical level lower than the lowermost extent of the barrier.

* * * * *